United States Patent [19]
Butt, Sr. et al.

[11] Patent Number: 5,492,751
[45] Date of Patent: Feb. 20, 1996

[54] DISPOSABLE GARMENT WITH IMPROVED CONTAINMENTS MEANS

[75] Inventors: Jon R. Butt, Sr., Woodstock; Christopher C. Creagan, Marietta; Cedric A. Dunkerly, II, Alpharetta; Richard S. Yeo, Dunwoody, all of Ga.

[73] Assignee: Kimberly-Clark Corporation, Neenah, Wis.

[21] Appl. No.: 205,684

[22] Filed: Mar. 2, 1994

Related U.S. Application Data

[63] Continuation-in-part of Ser. No. 65,210, May 20, 1993, abandoned.

[51] Int. Cl.$^6$ ..................................................... B05D 5/00
[52] U.S. Cl. .................... 428/198; 428/284; 604/370; 604/378; 604/385.1
[58] Field of Search .................... 428/198; 604/370, 604/378, 385.1

[56] References Cited

U.S. PATENT DOCUMENTS

| | | | |
|---|---|---|---|
| 3,799,167 | 3/1974 | Miller et al. | 128/287 |
| 3,934,587 | 1/1976 | Gordon | 128/284 |
| 3,989,867 | 11/1976 | Sisson | 428/132 |
| 4,041,203 | 8/1977 | Brock et al. | 428/157 |
| 4,341,217 | 7/1982 | Ferguson et al. | 128/290 |
| 4,356,229 | 10/1982 | Brodnyan et al. | 428/288 |
| 4,374,888 | 2/1983 | Bornslaeger | 428/198 |
| 4,374,894 | 2/1983 | Antlfinger | 428/288 |
| 4,405,325 | 2/1983 | Antlfinger et al. | 604/370 |
| 4,499,139 | 2/1985 | Schortmann | 428/245 |
| 4,578,071 | 3/1986 | Buell | 604/379 |
| 4,632,860 | 12/1986 | D'Antonio et al. | 428/290 |
| 4,676,786 | 6/1987 | Nishino | 604/378 |
| 4,695,278 | 9/1987 | Lawson | 604/385 |
| 4,704,107 | 11/1987 | Coates | 604/357 |
| 4,704,114 | 11/1987 | Wilson et al. | 604/385 |
| 4,704,116 | 11/1987 | Enloe | 604/385 |
| 4,766,029 | 8/1988 | Brock et al. | 428/286 |
| 4,846,823 | 7/1989 | Enloe | 604/385.2 |
| 4,846,825 | 7/1989 | Enloe et al. | 604/385.1 |
| 4,863,785 | 9/1989 | Berman et al. | 428/218 |
| 5,073,436 | 12/1991 | Antonacci et al. | 428/219 |
| 5,114,787 | 5/1992 | Chaplin et al. | 428/284 |
| 5,173,356 | 12/1992 | Eaton et al. | 428/219 |
| B1 4,636,207 | 11/1989 | Buell | 604/370 |

FOREIGN PATENT DOCUMENTS

| | | | |
|---|---|---|---|
| 0370835 | 5/1990 | European Pat. Off. | B32B 5/26 |
| 0569860 | 11/1993 | European Pat. Off. | D04H 1/54 |
| 2126162 | 3/1984 | United Kingdom | B32B 5/26 |

OTHER PUBLICATIONS

"Reifenhauser Develops Lightweight System", *Nonwovens Report* International, Jun. 1992, Issue No. 255, pp. 3–4.
Kokai Patent Application No. HEI 2[1990]–234967.

*Primary Examiner*—Christopher W. Raimund
*Attorney, Agent, or Firm*—William D. Herrick

[57] ABSTRACT

Disclosed is a lightweight nonwoven laminate particularly useful as a component of personal care articles, for example as a barrier cuff material for disposable diapers. Components of the laminate include at least one fine fiber layer having a basis weight in the range of from about 1.5 gsm to 26 gsm and at least one continuous filament layer having a basis weight in the range of from about 10 gsm to 30 gsm. The fine fiber component comprises at least a ratio of 5% and the layers are intermittently bonded for a total basis weight up to about 55 gsm. Desirable softness, breathability and barrier properties are obtained.

19 Claims, 2 Drawing Sheets

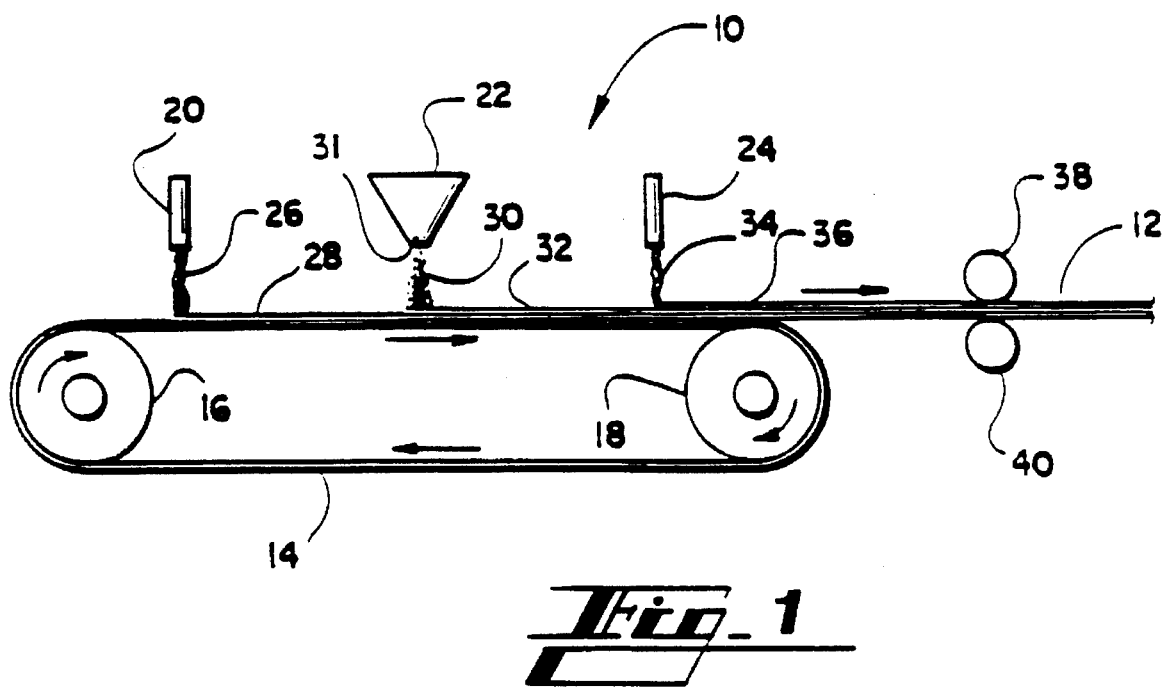
Fig_1
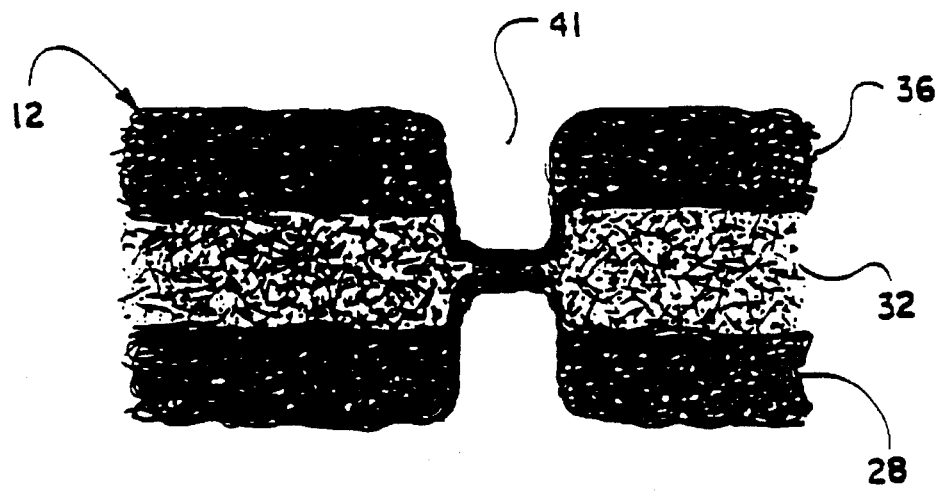
Fig_2

DISPOSABLE GARMENT WITH IMPROVED CONTAINMENTS MEANS

CROSS REFERENCE TO RELATED APPLICATIONS

This application is a continuation-in-part of U.S. patent application Ser. No. 08/065,210, filed May 20, 1993, now abandoned.

BACKGROUND OF THE INVENTION

Nonwoven fabric laminates are useful for a wide variety of applications. Such nonwoven fabric laminates are useful for wipers, towels, industrial garments, medical garments, medical drapes, and the like. In heavier basis weights the laminates are used in recreational applications such as tents and as car covers. Disposable fabric laminates have achieved especially widespread use in hospital operating rooms for drapes, gowns, towels, footcovers, sterilization wraps, and the like. Such surgical fabric laminates are generally spunbonded/meltblown/spunbonded (SMS) laminates consisting of nonwoven outer layers of spun-bonded polyolefins and an interior barrier layer of melt-blown polyolefins. Particularly, Kimberly-Clark Corporation, the assignee of the present invention, has for a number of years manufactured and sold SMS nonwoven surgical fabric laminates, sterilization wrap and recreational fabrics under the marks Spunguard® and Evolution®. Such SMS fabric laminates have outside spun-bonded layers which are durable and an internal melt-blown barrier layer which is porous but which, in combination with the spunbond layers, inhibits the strikethrough of liquids or the penetration of bacteria from the outside of the fabric laminate to the inside. In order for such a medical fabric to perform properly, it is necessary that the melt-blown barrier layer have a fiber size and a porosity that assures breathability of the fabric while at the same time inhibiting strikethrough of liquids.

Personal care absorbent articles such as disposable diapers, training pants, incontinent wear and feminine hygiene products utilize nonwoven fabrics for many purposes such as liners, transfer layers, absorbent media, backings, and the like. For many such applications the barrier properties of the nonwoven play an important role such as, for example, as containment flaps described in coassigned U.S. Pat. No. 4,704,116 to Enloe dated Nov. 3, 1987, incorporated herein in its entirety by reference. As described therein, disposable garments utilized for the absorption and containment of urine or other body exudates generally comprise a liquid pervious bodyside liner, a fluid impervious backing sheet with an absorbent material disposed therebetween and can be provided with improved containment by means of flaps. It is also desirable for personal care product applications such as containment flaps that the nonwoven fabric be soft and conformable and that the porosity of the fabric provide a level of breathability for increased comfort. As cost is always a factor, the ability to provide these benefits at low cost is another consideration.

Although nonwoven laminates having some combination of the properties desired have been available, they have not been widely utilized for applications such as the aforementioned flaps because one or more of the important considerations has been lacking or not present to a desired degree. The present invention is directed to improved nonwoven laminates satisfying those and other desired requirements.

Other objects and advantages of the invention will become apparent upon reading the following detailed description and upon reference to the drawings.

SUMMARY

The present invention is directed to improved nonwoven laminates which can be made in extremely light weights and include at least one fine fiber component layer and at least one continuous filament layer. The fine fiber layer includes fibers having an average diameter in the range of up to about 10 microns and a basis weight in the range of from about 1.5 gsm to about 26 gsm. The continuous filament web has filaments with an average diameter in the range of from about 12 microns to about 22 microns and a basis weight in the range of from about 5 gsm to about 30 gsm. The layers are bonded intermittently for a total basis weight not to exceed about 55 gsm and with the ratio of fine fibers to continuous filaments at least 5%. The resulting laminate has an improved combination of properties including softness and conformability as measured by a cup crush peak load test value no more than 150 g, cup crush test energy value of no more than 2250 g-mm, for certain applications a barrier as measured by hydrostatic head of at least 15 cm, and breathability as measured in terms of Frazier porosity of at least 50 scfm. Preferred embodiments are described below and include spunbond continuous filament webs and melt-blown fine fiber webs as the respective layers.

BRIEF DESCRIPTION OF THE DRAWINGS

FIG. 1 is a schematic diagram of a forming machine which is used in making the nonwoven fabric laminate including the melt-blown barrier layer of the present invention;

FIG. 2 is a cross-section view of the nonwoven fabric laminate of the present invention showing the layer configuration including the internal fine fiber barrier layer made in accordance with the present invention;

DETAILED DESCRIPTION OF THE INVENTION

Figure 3:
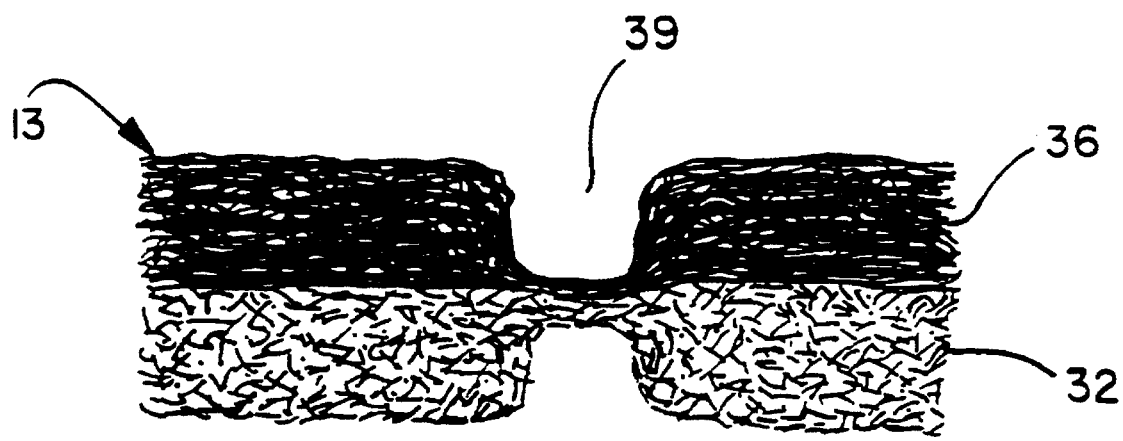
FIG. 3 is a cross-section view of an alternative embodiment of the nonwoven fabric laminate of the present invention in a two layer configuration.

While the invention will be described in connection with preferred embodiments, it will be understood that we do not intend to limit the invention to those embodiments. On the contrary, we intend to cover all alternatives, modifications, and equivalents as may be included within the spirit and scope of the invention as defined by the appended claims.

The present invention is directed to improved lightweight nonwoven laminates including at least one fine fiber component layer and at least one continuous filament layer. The fine fiber layer includes fibers having an average diameter in the range of up to about 10 microns and a basis weight in the range of from about 1.5 gsm to about 26 gsm. Advantageously for applications in disposable personal care products the average fine fiber diameter will be in the range of up to about 5 microns, and the fine fiber web basis weight will be in the range of from about 1.5 to about 10 gsm. The continuous filament web has filaments with an average diameter in the range of from about 12 microns to about 22 microns and a basis weight in the range of from about 10 gsm to about 30 gsm. Advantageously for disposable personal care product applications the continuous filaments have an average diameter in the range of from about 12 microns to about 18 microns and a basis weight in the range of from about 10 gsm to about 20 gsm. The layers are bonded intermittently for a total basis weight not to exceed about 55 gsm and with the amount of fine fibers based on the laminate weight of at least 5%. Advantageously for disposable personal care product applications the laminate basis weight in accordance with the invention is extremely low and within the range of up to about 20 gsm and the fine fibers constitute a low proportion of the laminate in the range of about 5% to about 25%. The resulting laminate has an improved combination of properties including softness and conformability as measured by a cup crush peak load test value no more than 150 g, when desired a barrier as measured by hydrostatic head of at least 15 cm, and breathability as measured in terms of Frazier porosity of at least 50 scfm. Preferred embodiments include spunbond continuous filament webs and meltblown fine fiber webs as the respective layers. On commercial equipment a three layer laminate has been made combining two continuous filament layers of 7.65 gsm each with a middle fine fiber layer of 1.7 gsm.

The foregoing objectives are preferably obtained by forming a melt-blown web in accordance with coassigned U.S. Pat. No. 5,213,881 to Timmons et al. dated May 25, 1993, incorporated herein in its entirety by reference, from a propylene polymer resin having a broad molecular weight distribution and having a high melt flow rate which resin is modified by the addition of a small amount of peroxide prodegradant prior to processing to achieve an even higher melt flow rate (lower viscosity). In general, the present invention may start with a propylene polymer in the form of reactor granules which polymer has a molecular weight distribution of 3.6 to 4.8 Mw/Mn, advantageously 3.6 to 4.0 Mw/Mn and a melt flow rate of about 400 gms/10 min to 3000 gms/10 min at 230° C. Such a molecular weight reactor granule polymer is then modified to reduce and narrow the polymer's molecular weight distribution to a range from 2.2 to 3.5 Mw/Mn by the addition of up to 3000 parts per million (ppm) of peroxide prodegradant. During the meltblowing process, the modified reactor granule polymer increases in melt flow rate from 400 gms/10 min. to 3000, for example, to a range between 800 up to 5000 gms/10 min at 230° C.

Particularly advantageous embodiments for disposable personal care applications include a polypropylene resin in the form of a reactor granule having a starting molecular weight distribution of 3.6 to 4.8 Mw/Mn and a melt flow rate of from 600 to 3000 gms/10 min. at 230° C. which is combined with a small amount of peroxide prodegradant, less than 500 ppm, to produce a modified polypropylene having a very high melt flow rate of up to 5000 gms/10 min. at 230° C. and a narrower molecular weight distribution of 2.8 to 3.5 Mw/Mn.

Alternatively, an improved fine fiber web for use as a barrier layer can be formed by utilizing a resin, particularly polypropylene, having a narrow molecular weight distribution and having a lower melt flow rate which resin is modified by the addition of a larger amount of peroxide prodegradant prior to melt-blowing to achieve a high melt flow rate. The starting reactor granule polypropylene resin in this case has a molecular weight distribution between 4.0 and 4.8 Mw/Mn and a melt flow rate ranging from 400 to 1000 gms/10 min. at 230° C. The polypropylene resin is modified by adding peroxide in amounts ranging from 500 to 3000 ppm (the higher amounts of peroxide being used in connection with the lower initial melt flow rate). The modified polypropylene resin has a melt flow rate, up to about 3000 gms/10 min. at 230° C. and a narrow molecular weight distribution of 2.2 to 2.8 Mw/Mn, for example.

As a specific example, the starting polypropylene resin for the fine fiber web of the lightweight nonwoven laminate of the present invention may be a polypropylene reactor granule which resin has a molecular weight distribution between 3.6 and 4.8 Mw/Mn, has a melt flow rate of up to 3000 gms/10 min. at 230° C., and is treated with about 500 ppm of peroxide to produce a modified resin having a melt flow rate greater than 2000 gms/10 min. at 230° C. and a molecular weight distribution of from 2.8 to 3.5 Mw/Mn. The broader molecular weight distribution at the high melt flow rate helps minimize production of lint and polymer droplets (shot).

Turning to FIG. 1, there is shown schematically a forming machine 10 which may be used to produce an improved nonwoven fabric laminate 12 having a fine fiber meltblown barrier layer 32 and outer continuous filaments layer 28 in accordance with the present invention. Particularly, the forming machine 10 consists of an endless foraminous forming belt 14 wrapped around rollers 16 and 18 so that the belt 14 is driven in the direction shown by the arrows. The forming machine 10 has three stations, spun-bond station 20, melt-blown station 22, and spun-bond station 24. It should be understood that more than three forming stations may be utilized to build up layers of higher basis weight. Alternatively, each of the laminate layers may be formed separately, rolled, and later converted to the fabric laminate off-line. In addition the fabric laminate 12 could be formed of more than or less than three layers depending on the requirements for the particular end use for the fabric laminate 12. For example, for some applications it may be preferred to have at least two inner meltblown layers for improved performance and for extremely lightweight applications a two-layer laminate may be made.

The spunbond stations 20 and 24 are conventional extruders with spinnerets which form continuous filaments of a polymer and deposit those filaments onto the forming belt 14 in a random interlaced fashion. The spun-bond stations 20 and 24 may include one or more spinnerets heads depending on the speed of the process and the particular polymer being used. Forming spunbonded material is conventional in the art, and the design of such a spunbonded forming station is thought to be well within the ability of those of ordinary skill in the art. The nonwoven spunbonded webs 28 and 36 are prepared in conventional fashion such as illustrated by the following patents: Dorschner et al. U.S. Pat. No. 3,692,618; Kinney U.S. Pat. Nos. 3,338,992 and 3,341,394; Levy U.S. Pat. No. 3,502,538; Hartmann U.S. Pat. Nos. 3,502,763 and 3,909,009; Dobo et al. U.S. Pat. No. 3,542,615; Harmon Canadian Patent No. 803,714; Matsuki et al., U.S. Pat. No. 3,802,817 and Appel et al. U.S. Pat. No. 4,340,563. Other methods for forming a nonwoven web having continuous filaments of a polymer are contemplated for use with the present invention.

Spunbonded materials prepared with continuous filaments generally have at least three common features. First, the polymer is continuously extruded through a spinneret to form discrete filaments. Thereafter, the filaments are drawn either mechanically or pneumatically without breaking in order to molecularly orient the polymer filaments and achieve tenacity. Lastly, the continuous filaments are deposited in a substantially random manner onto a carrier belt to form a web. Particularly, the spunbond station 20 produces spun-bond filaments 26 from a fiber forming polymer. The filaments are randomly laid on the belt 14 to form a spunbonded external layer 28. The fiber forming polymer is described in greater detail below.

The meltblown station 22 consists of a die 31 which is used to form microfibers 30. The throughput of the die 31 is specified in mounds of polymer melt per inch of die width per hour (PIH). As the thermoplastic polymer exits the die 31, high pressure fluid, usually air, attenuates and spreads the polymer stream to form microfibers 30. The microfibers 30 are randomly deposited on top of the spunbond layer 28 and form a meltblown layer 32. The construction and operation of the meltblown station 22 for forming microfibers 30 and meltblown layer 32 is considered conventional, and the design and operation are well within the ability of those of ordinary skill in the art. Such skill is demonstrated by NRL Report 4364, "Manufacture of Super-Fine Organic Fibers", by V. A. Wendt, E. L. Boon, and C. D. Fluharty; NRL Report 5265, "An Improved Device for the Formation of Super-Fine Thermoplastic Fibers", by K. D. Lawrence, R. T. Lukas, and J. A. Young; and U.S. Pat. No. 3,849,241, issued Nov. 19, 1974, to Buntin et al. Other methods for forming a nonwoven web of microfibers are contemplated for use with the present invention.

The meltblown station 22 produces fine fibers 30 from a fiber forming polymer which will be described in greater detail below. The fibers 30 are randomly deposited on top of spunbond layer 28 to form a meltblown internal layer 32. For a barrier flap fabric laminate, for example, the meltblown barrier layer 32 has a basis weight of commonly about 1.5 gsm to about 26 gsm, and advantageously for disposable personal care products from about 1.5 gsm to about 10 gsm.

After the internal layer 32 has been deposited by the meltblown station 22 onto layer 28, spun-bond station 24 produces spunbond filaments 34 which are deposited in random orientation on top of the melt-blown layer 32 to produce external spunbond layer 36. For a barrier flap fabric laminate for a disposable diaper, for example, the layers 28 and 36 each have a basis weight of commonly from about 5 gsm to about 30 gsm, more advantageously about 5 gsm to about 20 gsm.

The resulting SMS fabric laminate web 12 (FIG. 2) is then fed through bonding rolls 38 and 40. The surfaces of one or both of the bonding rolls 38 and 40 are provided with a raised pattern such as spots or grids. The bonding rolls are heated to the softening temperature of the polymer used to form the layers of the web 12. As the web 12 passes between the heated bonding rolls 38 and 40, the material is compressed and heated by the bonding rolls in accordance with the pattern on the rolls to create a pattern of discrete areas, such as 41 shown in FIG. 2, which areas are bonded from layer to layer and are bonded with respect to the particular filaments and/or fibers within each layer. Such discrete area or spot bonding is well-known in the art and can be carried out as described by means of heated rolls or by means of ultrasonic heating of the web 12 to produced discrete area thermally bonded filaments, fibers, and layers. In accordance with conventional practice described in Brock et al., U.S. Pat. No. 4,041,203, it is preferable for the fibers of the meltblown layer in the fabric laminate to fuse within the bond areas while the filaments of the spun-bonded layers retain their integrity in order to achieve good strength characteristics. For heavier basis weight laminates, for example, sonic bonding as described in U.S. Pat. No. 4,374,888, incorporated herein by reference, is preferred.

Figure 4:
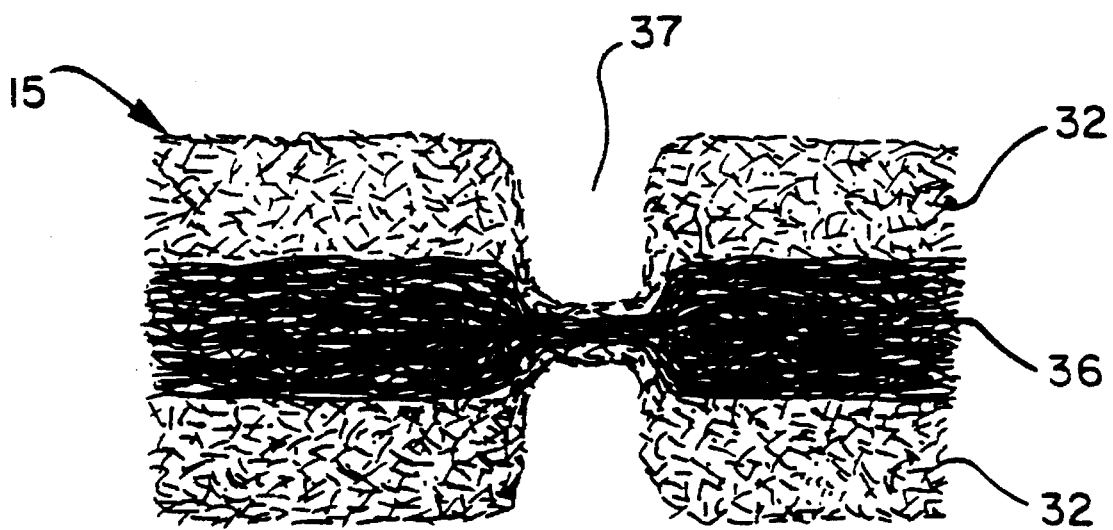
FIG. 4 is a cross-section view of a third embodiment of the nonwoven fabric laminate of the present invention with external fine fiber layers.

Turning to FIGS. 3 and 4, alternative embodiments are illustrated. FIG. 3 is a cross-section similar to FIG. 2 showing a two layer laminate 13 comprised of fine fiber layer 32 and continuous filament layer 36 combined by thermal bond 39. FIG. 4 is a similar view of an alternative three-layer embodiment 15 comprising outer fine fiber layers 32 with inner continuous filament layer 36 combined by thermal bond 37.

In accordance with the invention, the total basis weight of the laminate is in the range generally of up to about 55 gsm with heavier basis weights useful as recreational fabrics, more specifically up to about 34 gsm for applications such as wipes, medical fabric for sterilization wrappers, garments and drapes and the like, most advantageously up to about 20 gsm for personal care products and the amount of fine fibers compared to continuous filaments is at least about 5% generally, and more particularly up to about 25% based on total weight of fine fibers and continuous filaments although even higher proportions of fine fibers will be useful.

In accordance with the present invention, a preferred embodiment of a meltblown web formed in accordance with U.S. Pat. No. 5,213,881 to Timmons, Kobylivker and Woon dated May 25, 1993, incorporated herein by reference, is utilized as the fine fiber component or components.

The resulting meltblown web 32 with its fine fibers and resulting small pore size distribution has superior barrier properties when incorporated into a fabric laminate. Particularly, the unlaminated meltblown web 32 has an average fiber size of from 1 to 3 microns and pore sizes distributed predominantly in the range from 7 to 12 microns, with a lesser amount of pores from 12 to 25 microns, with virtually no pores greater than 25 microns, and with the peak of the pore size distribution less than 10 microns.

The present invention can be carried out with polyolefins including predominantly propylene polymer but which may include, polyethylene, or other alphaolefins polymerized with Ziegler-Natta catalyst technology, and copolymers, terpolymers, or blends thereof. Polypropylene is preferred for the continuous filament web.

EXAMPLE 1

A lightweight nonwoven laminate was produced generally in accordance with the teachings of U.S. Pat. No. 4,041,203 to Brock and Meitner dated Aug. 9, 1977, incorporated herein in its entirety by reference. An in-line process was utilized as shown in FIG. 1 where the initial layer of spunbond is laid on the forming wire followed by the meltblown layer and finally the final layer of spunbond. The target total basis weight of the fabric was between 25 gsm and 34 gsm with the meltblown making up from between 6 gsm and 12 gsm of the total. For this Example, equal amounts of spunbond were on each side of the meltblown web although not essential to the invention.

The three-layer laminate material was then bonded using a thermal-mechanical bonder as in the above-mentioned U.S. Pat. No. 4,041,203. As is preferred, a pattern bond roll with a percent bond area from 5 to 20%, target of 13%, and with a pin density from 50 to 350 pin/sq. in., target of 300/sq. in. was utilized. The temperature of the system was between 200° F. to 300° F. with a target of 250° F. Bonding pressure was set so that a uniform nip was maintained across the face of the unit.

In accordance with the foregoing an in-line SMS fabric was produced with a total weight of 29 gsm of which 25% was made up of meltblown. The spunbond polymer was Exxon PP3445 polypropylene and the meltblown was Exxon 3495G polypropylene, both of which are available from Exxon Chemical Company. The fabric was then bonded using a "wire weave" pattern roll that had a bond area of 13% with a pin density of 300 pin/sq. in. and was operated at a temperature of 250° F.

Table 1 illustrates the combination of properties obtained with the nonwoven laminate material of Example 1. Basis weight was determined in accordance with ASTM Standard Test D3775-9. Hydrostatic head was determined in accordance with Method 5514 Federal Test Methods STD No. 191A, also AATCC STD 127-1980. Frazier air porosity was determined in accordance with ASTM D737, also Federal Test Methods 5450 Standard No. 191A. Cup crush results were determined by measuring the peak load required for a 4.5 cm diameter hemispherically shaped foot to crush a 9"×9" piece of fabric shaped into an approximately 6.5 cm diameter opening by a 6.5 cm tall inverted cup while the cup shaped fabric was surrounded by an approximately 6.5 cm diameter cylinder to maintain a uniform deformation of the cup shaped fabric. The foot and the cup were aligned to avoid contact between the cup walls and the foot which could affect the peak load. The peak load was measured while the foot was descending at a rate of about 0.25 inch per second (15 inches per minute) utilizing a Model FTD-G-500 load cell (500 gram range) available from the Schaevitz Company, Tennsauken, N.J. which provides the energy value.

TABLE 1

| Fine Fiber Layer | |
| --- | --- |
| Composition | polypropylene |
| Average fiber diameter (microns) | 3 |
| Basis weight (gsm) | 7.2 |
| Continuous Filament Layers | |
| Composition | polypropylene |
| Average filament diameter (microns) | 21 |
| Basis weight (gsm-each) | 10.8 |
| Laminate | |
| Basis weight (gsm) | 28.82 |
| Frazier Porosity (SCFM) | 75 |
| Hydrostatic head (cm water) | 45 |
| Cup Crush Peak Load (g) | 70 |
| Cup Crush Energy (g-mm) | 1500 |

When incorporated into a personal care article as a barrier flap component, the laminate of Example 1 demonstrated highly desired functionality and perceived comfort.

EXAMPLES 2–14

A wide variety of spunbond-meltblown fabrics and spunbond-meltblown-spunbond fabrics were produced generally in accordance with the teachings of U.S. Pat. No. 4,041,203 to Brock and Meitner dated Aug. 9, 1977, incorporated herein in its entirety by reference. The composite fabrics were bonded to a bonding area of approximately 15% and pin density of 120 pin/sq. in. The spunbond continuous fiber layer was preformed using apparatus generally as described in U.S. Pat. No. 3,802,817 to Matsuki et al. The continuous fibers were thermally bonded with a bonding area of approximately 15% and pin density of 120 pin/sq. in. The bonded continuous fiber layers were then fed on a formation wire of a meltblown machine where a layer of fine fibers was formed onto the continuous fiber layer to make continuous fiber layer—fine fiber layer laminate composites. The continuous fibers were made of polypropylene resin Exxon PP 3445 available from Exxon Chemical Company of Houston, Tex. PP3445 resin has a melt flow rate of 35 g/10 min. at 230° C. The fine fibers were made of polypropylene resin Himont PF015 supplied by Himont USA, Inc. of Wilmington, Del. PF015 resin has a melt flow rate of 400 g/10 min. at 230° C.

For the purposes of comparison, fabrics consisted of polypropylene continuous fibers both made by using processes described in U.S. Pat. No. 3,692,619 to Dorschner (Examples 12–14) and an apparatus of the type described in U.S. Pat. No. 3,802,817 to Matsuki et al. (Examples 9–11) were included in the following Table.

The process conditions for making the continuous fibers are given as in the following Table:

| | |
| --- | --- |
| Melt temperature: | 460° F. |
| Quench distance: | 45" |
| Quench delay: | 3" |
| Forming distance: | 9" |
| Thruput: | 0.6 g/hole/min |
| Spin-plate die hole: | 100 hole/in |

The process conditions for making the fine fibers are given as in the following Table:

| | |
| --- | --- |
| Forming distance: | 8 inch |
| Primary air flow: | 350 SCFM |
| Primary air temperature: | 520 degree F. |
| Melt temperature: | 520 degree F. |
| Thruput: | 2 pound/inch/hr |

TABLE 2

| Example Number | Description | | Average pore size (Micron) | FI$^1$ SB-up | FI$^2$ MB-up | Frazier Porosity |
| --- | --- | --- | --- | --- | --- | --- |
| | SB gsm | MB gsm | | | | |
| 2 | 27.1 | 3.4 | 34 | 14.4 | 14.4 | 284 |
| 3 | 27.1 | 1.7 | | 15.9 | 15.1 | 365 |
| 4 | 20.3 | 3.4 | | 12.1 | 12.1 | 325 |
| 5 | 20.3 | 1.7 | 43 | 14.0 | 13.4 | 403 |
| 6 | 13.6 | 6.8 | 21 | 10.5 | 11.2 | 197 |
| 7 | 13.6 | 3.4 | 31 | 14.8 | 14.3 | 363 |
| 8 | 13.6 | 1.7 | 34 | 16.0 | 16.2 | 453 |
| Comparative SB Fabrics | | | | | | |
| 9 | 13.6 | | 82 | 19.1 | | |
| 10 | 17.0 | | | 17.5 | | |
| 11 | 20.3 | | 71 | 15.6 | | |
| 12 | 27.1 | | | 19.1 | | 545 |
| 13 | 20.3 | | | 21.9 | | |
| 14 | 13.6 | | | 23.3 | | |

$^1$Formation index measured with fabric spunbond layer side up
$^2$Formation index measured with fabric meltblown layer side up For Examples 3, 4, 11 and 12, cup crush testing was also done with the following results: Example 3—peak load, 31 g and energy 539 g-mm; Example 4—peak load, 45 g and energy, 771 g-mm; Example 11—peak load, 48 g and energy 855 g-mm; and Example 12, peak load 32 g and energy, 603 g-mm.

EXAMPLES 15–20

Additional spunbond-meltblown webs and spunbond-meltblown-spunbond webs were made using a process described in U.S. Pat. No. 5,213,881 to Timmons et al. A spunbond layer was first formed onto the forming wire by using a spunbond process generally as described in U.S. Pat. No. 3,802,817 to Matsuki et al., followed by a fine fiber layer made by using a conventional meltblown process. Another layer of similar spunbond continuous fibers was formed onto the meltblown layer. The continuous fiber layers and fine fiber layer were thermally bonded together at a bonding area of approximately 15% and pin density of 250 pin/sq. in. The continuous fibers (spunbond layer) were made of polypropylene resin PP 3445 from Exxon. The fine fibers were made of polypropylene resin PF015 from Himont except sample 16 which was made of polypropylene resin HH416 from Himont. HH416 resin has a melt flow rate of 800 g/10 min. at 230° C.

TABLE 3

| Example Number | Description | | | Frazier Porosity |
|---|---|---|---|---|
| | SB gsm | MB gsm | SB gsm | |
| 15 | 13.6 | 13.6 | | |
| 16 | 13.6 | 6.8 | | |
| 17 | 10.2 | 10.2 | | |
| 18 | 10.2 | 13.6 | 10.2 | |
| 19 | 6.8 | 10.2 | 6.8 | 270 |
| 20 | 5.1 | 6.8 | 5.1 | 150 |

For Examples 19 and 20 cup crush testing was also done with the following results: Example 19—peak load, 76 g and energy 1351 g-mm; Example 20—peak load, 20 g and energy, 304 g-mm.

EXAMPLES 21–29

Additional spunbond-meltblown fabrics having varying basis weights were made as in Examples 15–20. The continuous fibers were made of polypropylene resin Exxon PP 3445 available from Exxon Chemical Company of Houston, Tex. while the fine fibers were made of polypropylene resin Himont PF015 available from Himont USA, of Wilmington, Del. PP 3445 resin has a melt flow rate of 35 g/10 min. at 230° C. while PF015 resin has a melt flow rate of 400 g/10 min. at 230° C.

The process conditions for the production of these fabrics are given in the following Table 4.

TABLE 4

| | Spunbond | Meltblown |
|---|---|---|
| Forming distance (in) | 12 | 9.5 |
| Melt temperature (°F.) | 439 | 494 |
| Quench/primary air flow (SCFM) | 45 (per inch) | 400 |
| Quench/primary air temperature (°F.) | 56 | 374 |
| Thruput | 1.23 GHM[1] | 4.6 PIH[2] |
| Spin-plate die holes/inch | 40 | 30 |
| Fume exhaust (% open) | 10 | N/A |
| Manifold pressure (psi) | 6 | N/A |

[1]GHM: g/hole/min
[2]PIH: pound/inch/hr

The line speed was 663 ft/min. The meltblown die/air plate set-up was 0.090 inch setback with 0.148 inch air gap.

The continuous fiber layer and fine fiber layer were then thermally bonded together having a bonding area of approximately 15% and pin density of 120 pin/sq. in. The fabrics were then further treated with surfactant Triton X-102 available from the Industrial Chemicals Division of Union Carbide Chemicals and Plastics Company of Danbury, Conn. The add-on level of the surfactant was approximately 0.3% of the fabric. For comparison, a fabric consisted of only continuous fibers made from the same machine and treated with Triton X-102 was included in the following Table 5.

TABLE 5

| Example Number | Description | | | Cup Crush | |
|---|---|---|---|---|---|
| | SB gsm | MB gsm | SB gsm | Peak Load g | Energy g-mm |
| 21 | 20.3 | 3.4 | | | |
| 22 | 17.0 | 3.4 | | | |
| 23 | 13.6 | 3.4 | | | |
| 24 | 17.0 | 1.7 | | | |
| 25 | 17.0 | 6.8 | | | |
| 26 | 13.6 | 1.7 | | | |
| 27 | 13.6 | 6.8 | | 43 | 770 |
| 28 | 20.3 | 1.7 | | | |
| 29 | 20.3 | | | 48 | 855 |

As another comparison, material produced in accordance with Example 4 of U.S. Pat. No. 5,213,081 to Timmons et al. was subjected to cup crush peak load and energy tests. The peak load was 229 g and the energy was 4992 g-mm indicating that laminates of the present invention are softer and maintain excellent strength properties.

From the foregoing Examples 1–29 it is apparent that the present invention, when compared with more conventional fabrics provides advantages in comfort without sacrificing strength and barrier properties. More specifically, with reference to Examples 1, 6 and 27, it can be determined that the nonwoven web laminates of the present invention have low cup crush values while, at the same time, are highly uniform, porous (breathable), have low pore sizes and possess good barrier properties (low Frazier values).

TEST METHODS

1. Web Formation Uniformity

The fabric uniformity is indicated by the "Formation Index" as measured by automatic image analysis technique. The measurement method consists of developing a grey level histogram from about 15 fields of view of wrinkle-free samples of the test fabric. Each field is of equal size and has dimensions of about 8"×10". Grey level measurements are made using a 20 mm Nikon lens mounted on a Chalnicon scanner interfaced to a Quantimet 970 Image Analyzer manufactured by Leica, Inc. of Deerfield, Ill. The fabric samples were placed on top of a flat black background consisting of black photodrape cloth or the like and illuminated with omnidirectional inclined darkfield light at an illumination angle of about 45°. A histogram accumulated over the 15 fields is developed from the grey level measurements. The Formation Index is defined as the percent coefficient of variation (100×standard deviation/mean) of the grey levels as determined from the composite grey level histogram. A low Formation Index indicates that the test fabric is more uniform than a comparable fabric having a higher Formation Index.

For two layer composite fabrics consisting of a layer of spunbond and a layer of meltblown, the Formation Index was measured both with spunbond side up meltblown side up.

2. Pore Size Determination For Examples 2–29

The average pore size of the sample web was determined by using a Coulter porometer manufactured by Coulter Electronics Ltd. of Luton, Beds, England. The technique employed by the Porometer is based on the liquid displacement method. The test sample was thoroughly wetted by a low surface tension liquid (Coulter Porofil, a fluorinated hydrocarbon). Air pressure was applied to one side of the sample. As the pressure increases, the liquid in large pores, followed by smaller pores, will be forced out allowing the air to pass through. The pore size distribution for each sample was then calculated from the applied pressure using the Washburn equation. The average pore size was calculated from the pore size distribution data.

Thus, in accordance with the invention there has been described an improved lightweight nonwoven laminate. Variations and alternative embodiments will be apparent to those skilled in the art and are intended to be embraced within the appended claims.

We claim:

1. In a disposable garment utilized for the absorption and containment of urine or other body exudates comprising a liquid pervious bodyside liner, a fluid impervious backing sheet with an absorbent material disposed therebetween and having flap means for enhanced containment, the improvement wherein the means for enhanced containment comprises a nonwoven fabric laminate comprising:

a) a nonwoven component layer comprising fine fibers having an average diameter in the range of up to about 10 microns and a basis weight of at least about 1.5 gsm, and b) a nonwoven component layer comprising continuous filaments having an average diameter in the range of from about 12 microns to about 22 microns and a basis weight of at least about 5 gsm, wherein said layers are intermittently bonded in a face-to-face relationship for a total basis weight not to exceed about 55 gsm and the percent of the weight of fine fibers layer to the laminate weight is at least 5%, and wherein said laminate has a cup crush peak load value of no more than 150 grams, a cup crush energy value of no more than 2250 g-mm, and a Frazier porosity of at least 50 scfm.

2. The disposable garment of claim 1 wherein the continuous filament component layer of said nonwoven fabric laminate comprises a propylene polymer.

3. The disposable garment of claim 2 wherein the fine fiber component layer of said nonwoven fabric laminate comprises a propylene polymer having a molecular weight distribution between 3.6 and 4.8 Mw/Mn and a melt flow rate up to about 3000 g/10 min. at 230° C.

4. The disposable garment of claim 1 wherein said nonwoven fabric laminate comprises two continuous filament layers on opposite sides of a fine fiber layer and said total basis weight does not exceed about 34 gsm.

5. The disposable garment of claim 2 wherein said nonwoven fabric laminate comprises two continuous filament layers on opposite sides of a fine fiber layer and said total basis weight does not exceed about 34 gsm.

6. The disposable garment of claim 3 wherein the ratio of the fine fibers to continuous filaments is up to about 25%.

7. The disposable garment of claim 1 as a diaper wherein said nonwoven fabric laminate comprises a containment flap.

8. The disposable garment of claim 4 as a diaper wherein said nonwoven fabric laminate comprises a containment flap.

9. The disposable garment of claim 6 as a diaper wherein said nonwoven fabric laminate comprises a containment flap.

10. The disposable garment of claim 1 wherein said nonwoven fabric laminate has a hydrostatic head of at least 15 cm.

11. The disposable garment of claim 3 wherein said nonwoven fabric laminate has a hydrostatic head of at least 15 cm.

12. The disposable garment of claim 4 wherein said nonwoven fabric laminate has a hydrostatic head of at least 15 cm.

13. The disposable garment of claim 1 wherein said nonwoven fabric laminate total basis weight does not exceed about 34 gsm.

14. The disposable garment of claim 1 wherein said nonwoven fabric laminate total basis weight does not exceed about 20 gsm.

15. The disposable garment of claim 4 wherein said nonwoven fabric laminate total basis weight does not exceed about 20 gsm.

16. The disposable garment of claim 5 wherein said nonwoven fabric laminate total basis weight does not exceed about 20 gsm.

17. The diaper of claim 7 wherein said nonwoven fabric laminate total basis weight does not exceed about 20 gsm.

18. The diaper of claim 8 wherein said nonwoven fabric laminate total basis weight does not exceed about 20 gsm.

19. The diaper of claim 9 wherein said nonwoven fabric laminate total basis weight does not exceed about 20 gsm.

* * * * *

UNITED STATES PATENT AND TRADEMARK OFFICE
CERTIFICATE OF CORRECTION

PATENT NO. : 5,492,751

DATED : February 20, 1996

INVENTOR(S) : J. R. Butt, Sr. et al.

It is certified that error appears in the above-identified patent and that said Letters Patent is hereby corrected as shown below:

Cover page, item (54) "CONTAINMENTS" should read --CONTAINMENT--;

Column 1, line 2, "CONTAINMENTS" should read --CONTAINMENT--;

Column 4, line 43, "spinnerets heads" should read --spinneret heads--;

Column 5, line 7, "mounds of polymer" should read --pounds of polymer--.

Signed and Sealed this

Third Day of September, 1996

Attest:

BRUCE LEHMAN

Attesting Officer     Commissioner of Patents and Trademarks